United States Patent
Hayashi et al.

(10) Patent No.: US 6,403,820 B1
(45) Date of Patent: Jun. 11, 2002

(54) PROCESS FOR PREPARING LOW-ACID-VALUE PHOSPHORIC ESTERS

(75) Inventors: Kazuhiko Hayashi; Tetsuo Kamimoto; Hisashi Murase; Ryoji Kimura, all of Saitama (JP)

(73) Assignee: Asahi Denka Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/762,566

(22) PCT Filed: Jun. 7, 2000

(86) PCT No.: PCT/JP00/03693

§ 371 (c)(1), (2), (4) Date: Feb. 8, 2001

(87) PCT Pub. No.: WO00/75149

PCT Pub. Date: Dec. 14, 2000

(30) Foreign Application Priority Data

Jun. 9, 1999 (JP) .......................................... 11-162933

(51) Int. Cl.[7] ................................................. C07F 9/02
(52) U.S. Cl. ...................................................... 558/147
(58) Field of Search ......................................... 558/147

(56) References Cited

U.S. PATENT DOCUMENTS 5,616,768 A * 4/1997 Kawata et al. .............. 558/146

FOREIGN PATENT DOCUMENTS

| JP | 8-67685 | 3/1996 |
| JP | 8-67695 | 3/1996 |
| JP | 2000-239285 | 9/2000 |

* cited by examiner

*Primary Examiner*—Floyd D. Higel
*Assistant Examiner*—Ebenezer Sackey
(74) *Attorney, Agent, or Firm*—Young & Thompson

(57) ABSTRACT

The process for producing a low acid value phosphoric ester of the present invention is characterized by comprising treating a phosphoric ester having an acid value with an organic ortho-acid ester. The phosphoric ester preferably has a specific structure. The organic ortho-acid ester is preferably an ester of orthoformic acid, orthoacetic acid or orthopropionic acid with an alkyl group having 1 to 4 carbon atoms.

10 Claims, No Drawings

PROCESS FOR PREPARING LOW-ACID-VALUE PHOSPHORIC ESTERS

This application is a 371 of PCT/JP00/03693 filed Jun. 7, 2000.

TECHNICAL FIELD

The present invention relates to a process for producing a phosphoric ester of low acid value. More particularly, it relates to a process for obtaining a phosphoric ester having a low acid value and excellent physical properties, such as heat resistance, storage stability, and hydrolysis resistance. The phosphoric ester obtained is useful as a plasticizer or a flame retardant for synthetic resins.

BACKGROUND ART

It is known that phosphoric esters are synthesized by processes comprising dehydrochlorination reaction between phosphorus oxychloride and an alcohol or a phenol. Because these processes do not accomplish perfect esterification, however, the resulting phosphoric esters have an acid value ascribed to a phosphoric acid radical or an acid chloride derived from the starting material. Phosphoric esters having an acid value are not satisfactory in heat resistance, hydrolysis resistance, and storage stability. When exposed to high temperature, they undergo considerable coloration and, when added to a resin as a flame retardant, invite reductions of the physical properties of the resin and coloration of the resin. Phosphoric esters having an acid value have another problem that they corrode a mold for molding the resin. To avoid these problems, it is desirable to control the acid value of phosphoric esters to 1.0 (mg/KOH) or smaller.

In order to obtain a phosphoric ester of low acid value, it has been a generally followed practice that a phosphoric ester is purified by neutralization with a basic substance, for example, in a wet process using an alkali metal hydroxide such as sodium hydroxide or in a dry process using an alkali metal compound such as calcium carbonate or magnesium hydroxide, followed by washing with water or distillation.

However, where a phosphoric ester having a high viscosity is purified, the wet neutralization with an alkali metal hydroxide meets difficulty in separation between an aqueous layer and an oily layer, which not only needs a long process time but results in incorporation of a trace amount (e.g., several ppm to several hundreds of ppm) of the alkali metal into the oily layer separated. If any alkali metal remains in the purification step of phosphoric esters, it adversely affects the heat resistance and hydrolysis resistance of the phosphoric esters and causes reductions of physical properties of some kinds of resins, such as a change in composition.

For the purpose of reducing the residual alkali metal content, a phosphoric ester may be diluted with an organic solvent to reduce the viscosity or subjected to salting out to improve separation into an aqueous layer and an oily layer. Nevertheless these manipulations still allow a trace amount of the alkali metal to remain in the product layer. Therefore, removal of the alkali metal is usually conducted by washing several times. The same problem arises in the case of dry neutralization.

Some phosphoric esters are not suitable to be wet neutralized with alkali metals because they get emulsified on wet neutralization and cannot be separated into an aqueous layer and a product layer.

Purification of phosphoric esters by distillation is also adopted. Purification by distillation is freed of the above-described problem of alkali metal remaining with respect to phosphoric esters having a low molecular weight but requires a distillation apparatus having a high fractionation effect, such as a rectifier, in order to remove impurities other than alkali metals which will reduce the physical properties of phosphoric esters (for example, heat resistance, storage stability and hydrolysis resistance). There is another problem that distillation purification is more difficult with a phosphoric ester having a larger molecular weight. Further, distillation purification has a poor yield, resulting in an increased cost of the phosphoric ester.

Japanese Patent Laid-Open No. 67685/96 discloses a process of producing a phosphoric ester, which comprises treating a crude phosphoric ester with an epoxy compound, followed by heat treatment in the presence of water. However, this process involves heat treatment in the presence of water (hereinafter "water/heat treatment") after epoxy treatment, which makes the steps complicated. Further, should the water/heat treatment be insufficient, the product is deteriorated in both acid value and hue. Even when the water/heat treatment is sufficient, the product is unsatisfactory in hue and storage stability.

Accordingly, an object of the present invention is to provide a process for producing a phosphoric ester having a low acid value and excellent in heat resistance, hydrolysis resistance and storage stability.

DISCLOSURE OF THE INVENTION

The above object of the invention is accomplished by a process for producing a low acid value phosphoric ester characterized by treating a phosphoric ester having an acid value with an organic ortho-acid ester.

BEST MODE FOR CARRYING OUT THE INVENTION

The process of producing a low acid value phosphoric ester according to the present invention will be described in detail.

The phosphoric esters which can be treated by the process of the present invention are known in the art usually for use as plasticizers and/or flame retardants for resins. As far as they have such acid values as have to be reduced, the kinds, the process of making and the like are not particularly limited. Typical examples of the phosphoric esters used in the present invention are those represented by general formula (1):

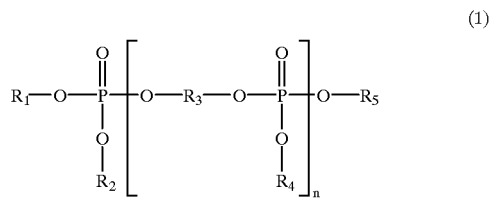

(1)

wherein $R_1$, $R_2$, $R_4$, and $R_5$, which may be the same or different, each represent an alkyl group having 1 to 10 carbon atoms or an aromatic group represented by general formula (2) shown below; $R_3$ represents a divalent aromatic group represented by general formula (3) or (4) shown below; and n represents 0 to 30.

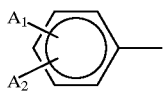

(2)

wherein $A_1$ and $A_2$ each independently represent a hydrogen atom or an alkyl group having 1 to 10 carbon atoms.

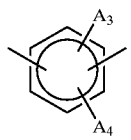

(3)

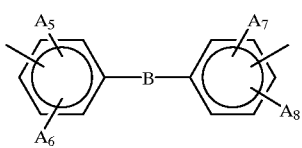

(4)

wherein $A_3$, $A_4$, $A_5$, $A_6$, $A_7$, and $A_8$ each independently represent a hydrogen atom, an alkyl group having 1 to 4 carbon atoms, a cycloalkyl group, an aryl group, an alkoxy group, a nitro group, a halogen atom or a cyano group; and B represents a single bond, divalent S, a sulfone group, or an alkylidene or alkylene group having 1 to 5 carbon atoms.

In general formulae (1) and (2), the alkyl group as represented by $R_1$, $R_2$, $R_4$, $R_5$, $A_1$, and $A_2$ includes methyl, ethyl, propyl, isopropyl, butyl, isobutyl, sec-butyl, tert-butyl, amyl, tert-amyl, hexyl, 2-ethylhexyl, n-octyl, nonyl, and decyl. The alkyl group having 1 to 4 carbon atoms as represented by $A_3$, $A_4$, $A_5$, $A_6$, $A_7$, and $A_8$ includes methyl, ethyl, propyl, butyl, isobutyl, sec-butyl, and tert-butyl. The cycloalkyl group includes cyclohexyl. The aryl group includes phenyl, cresyl, xylyl, 2,6-xylyl, 2,4,6-trimethylphenyl, butylphenyl, and nonylphenyl. The alkoxy group includes methoxy, ethoxy, propoxy, and butoxy. The halogen atom includes a fluorine atom, a chlorine atom, and a bromine atom. The group represented by general formula (2) includes phenyl, cresyl, xylyl, 2,6-xylyl, butylphenyl, and nonylphenyl. The alkylidene group having 1 to 5 carbon atoms as represented by B includes ethylidene and 2,2'-propylidene. The alkylene group includes methylene, ethylene, trimethylene, and tetramethylene.

The acid value of a phosphoric ester to which the process of the present invention is applied includes one attributed to the acid radical remaining after the synthesis of the phosphoric ester and one attributed to the acid radical produced during storage.

The above-described phosphoric esters which can be used in the process of the present invention can be obtained by methods known in the art. They are usually obtained by allowing phosphorus oxychloride to react with an appropriate alcohol or phenol in the absence or presence of a catalyst such as a Lewis acid (e.g., aluminum chloride, magnesium chloride or titanium tetrachloride). Specifically, a phosphoric triester is produced by allowing phosphorus oxychloride to react with a phenol in the presence of a Lewis acid catalyst (see, e.g., G. Jacobsen, Ber. 81519 (1875) and M. Rapp, Ann. 224 156 (1884)). An aromatic bisphosphate is obtained by allowing phosphorus oxychloride to react with an aromatic monohydroxy compound (a monohydric phenol) in the presence of a Lewis acid catalyst and allowing the resulting diarylphosphorohalidate to react with an aromatic dihydroxy compound (a dihydric phenol) in the presence of the same catalyst (see, e.g., Japanese Patent. Laid-Open No. 1079/93). An aromatic diphosphate is also obtainable by allowing phosphorus oxychloride to react with a dihydroxy compound, removing the unreacted phosphorus oxychloride, and allowing the product to react with an aromatic monohydroxy compound (see Japanese Patent Laid-Open No. 227632/88). An aromatic diphosphate is also obtainable by allowing phosphorus oxychloride to react with a mixture of a monohydroxy compound and a dihydroxy compound.

Preferred examples of the alcohols which can be used for the production of the phosphoric esters include aliphatic alcohols, such as methanol, ethanol, n-propyl alcohol, isopropyl alcohol, n-butyl alcohol, octyl alcohol, 2-ethylhexyl alcohol, capryl alcohol, nonyl alcohol, and n-decyl alcohol; alicyclic alcohols, such as cyclohexanol; and aromatic alcohols, such as benzyl alcohol.

Preferred examples of the phenols which can be used in the production of the phosphoric esters include phenol, cresol, xylenol, resorcin, hydroquinone, bisphenol A, tetrabisphenol A, bisphenol F, bisphenol S, biphenol, and naphthol.

The reaction conditions for preparing the phosphoric esters, such as the amount of the reaction catalyst, the reacting ratio of phosphoric acid and the alcohol or phenol, the reacting ratio of phosphorus oxychloride and the alcohol or phenol, the reaction temperature, and the reaction time, can be decided appropriately within known ranges.

Specific examples of the phosphoric esters of general formula (1) in which n is 0 are triphenyl phosphate, tricresyl phosphate, diphenyl-2-ethylcresyl phosphate, tri(isopropylphenyl) phosphate, methyldiphenyl phosphate, phenyldiethyl phosphate, diphenylcresyl phosphate, and tributyl phosphate. Those in which n is 1 or greater include phenyl.bisphenolA.polyphosphate, cresyl.bisphenolA.polyphosphate, phenyl.cresyl.bisphenolA.polyphosphate, xylyl.bisphenolA.polyphosphate, phenyl-p-t-butylphenyl.bisphenolA.polyphosphate, phenyl.isopropylphenyl-bisphenolA.polyphosphate, phenyl.resorcin.polyphosphate, cresyl.resorcin.polyphosphate, phenyl.cresyl.resorcin.polyphosphate, xylyl.resorcin.polyphosphate, phenyl-p-t-butylphenyl-resorcin-polyphosphate, and phenyl.isopropylphenyl.resorcin.polyphosphate.

While the production process of the present invention is applicable to any of the above-described phosphoric esters, particularly pronounced effects are produced in application to the phosphoric esters of general formula: (1) in which n is 1 or greater, which have large molecular weights and are difficult to purify by general treating methods.

Of the phosphoric esters in which n is I or greater, (a) those of general formula (1) wherein $R_1$, $R_2$, $R_4$, and $R_5$ are each the group represented by general formula (2), $R_3$ is the group represented by general formula (4), and B is 2,2'-propylidene; especially (a') those wherein $A_1$ and $A_2$ in the group represented by general formula (2) and $A_5$, $A_6$, $A_7$, and $A_8$ in the group represented by general formula (4) are each a hydrogen atom; and (b) those of general formula (1) wherein $R_1$, $R_2$, $R_4$, and $R_5$ are each the group represented by general formula (2), and $R_3$ is the group represented by general formula (3) enjoy particularly outstanding effects when the production process of the present invention is applied thereto.

The phosphoric esters thus produced usually contain considerable impurities. They are subjected to acid treatment with hydrochloric acid, etc. and refluxing dehydration to remove the impurities. The production process of the present invention is for effective reduction of the acid value of the thus obtained phosphoric esters.

The above-mentioned phosphoric esters include solid ones and liquid ones. While the production process of the present invention is applicable to both of them, it is preferred that a crude phosphoric ester which is solid be used as dissolved in a solvent. Any solvent can be used here as long as it is capable of dissolving the crude phosphoric ester and does not interfere with the action of an organic ortho-acid ester that is assumed to be as described later. Specific examples of the solvents include aromatic solvents, such as toluene, xylene, and dichlorobenzene, aliphatic solvents, such as hexane and heptane, and alicyclic solvents, such as cyclohexane. Preferred of them are aromatic solvents because of their satisfactory capability of dissolving crude phosphoric esters. In the present invention, it is unfavorable to use a hydroxyl-containing alcoholic compound or an amino-containing compound as a solvent for dissolving a crude phosphoric ester. The reason is that, for one thing, these compounds, while being heat treated, undergo interesterification with a phosphoric ester to be purified to reduce the purity or reaction with impurities to form salts and, for another, they are likely to react with the organic ortho-acid ester.

In the production process of the present invention, the phosphoric ester having an acid value is treated with an organic ortho-acid ester. The treatment with an organic ortho-acid ester according to the present invention is to esterify the acid component in the impurities present in the phosphoric ester having an acid value with the organic ortho-acid ester.

Examples of preferred organic ortho-acid esters include alkyl esters and aromatic esters of organic ortho-acids, such as orthoformic acid, orthoacetic acid, and orthopropionic acid. Specific examples are trimethyl orthoformate, triethyl orthoformate, tributyl orthoformate, trimethyl orthoacetate, triethyl orthoacetate, tributyl orthoacetate, trimethyl orthopropionate, triethyl orthopropionate, tributyl orthopropionate, and triphenyl orthoformate.

Particularly preferred of them are esters of orthoformic acid, orthoacetic acid or orthopropionic acid with an alkyl group having 1 to 4 carbon atoms because they have a small molecular weight and, therefor, an excess of them can easily be removed by distillation.

While any of the above-described organic ortho-acid esters can be used in the present invention, it is economically preferred to use organic ortho-acid esters that are liquid at ambient temperature. Examples of organic ortho-acid esters that are liquid at ambient temperature are trimethyl orthoformate, triethyl orthoformate, tributyl orthoformate, trimethyl orthoacetate, triethyl orthoacetate, tributyl orthoacetate, trimethyl orthopropionate, triethyl orthopropionate, and tributyl orthopropionate. It is still preferred to use trimethyl orthoformate, triethyl orthoformate, trimethyl orthoacetate or triethyl orthoacetate, which have a molecular weight of from 100 to 500. Excess of an organic ortho-acid ester having a large molecular weight is difficult to remove by distillation. When an organic ortho-acid ester having a small molecular weight is used, excess can easily be removed by distillation.

The manner of treating the phosphoric ester having an acid value with the organic ortho-acid ester is not particularly restricted and appropriately selected according to the physical properties or reactivity, etc. of the organic ortho-acid ester used. For example, when the phosphoric ester having an acid value is treated with liquid triethyl orthoformate, the treatment can be carried out by adding the organic ortho-acid triethyl ester to the phosphoric ester followed by heating.

The temperature for treating the phosphoric ester having an acid value with the organic ortho-acid ester is decided appropriately depending on the kind of the organic ortho-acid ester used. In using triethyl orthoformate, for example, a preferred temperature is 50° C. to 160° C., particularly 80° C. to 140° C., with the reactivity and a volatilization loss of triethyl orthoformate taken into consideration. At reaction temperatures lower than 50° C., it is likely that the organic ortho-acid ester exhibits insufficient reactivity and needs an extended reaction time and that an insufficient reaction results in a failure to completely remove impurities after the treatment of the phosphoric ester with the organic ortho-acid ester. On the other hand, treating temperatures above 160° C. exceed the boiling point of the organic ortho-acid ester, resulting in reduction of the reaction efficiency.

The time for treating the phosphoric ester having an acid value with the organic ortho-acid ester is decided appropriately according to the kind and the molecular weight of the organic ortho-acid ester used and the reaction temperature. In general, the treating time is preferably about 10 minutes to 3 hours. In using, for example, triethyl orthoformate having a molecular weight of about 148, a preferred treating tithe is 1 to 2 hours.

In treating the phosphoric ester having an acid value with the organic ortho-acid ester, it is theoretically sufficient for the organic ortho-acid ester to be added to the phosphoric ester in an amount corresponding to the acid value of the phosphoric ester. It is preferred however that the organic ortho-acid ester be added in slight excess over the amount corresponding to the acid value of the phosphoric ester from the considerations for the reactivity of the organic ortho-acid ester, the residual water content in the phosphoric ester, and a volatilization loss of the organic ortho-acid ester in case where it has a low boiling point. In general, the ratio of the phosphoric ester to the organic ortho-acid ester added is preferably about 1:1 to about 1:20 by mole based on the acid value of the crude phosphoric ester.

While not having been confirmed, it is assumed that the following reaction takes place while a phosphoric ester having an acid value is treated with an organic ortho-acid ester according to the process of the present invention. It is considered that the acid components present in the phosphoric ester having an acid value are, esterified with the organic ortho-acid ester in the treatment, whereby the acid value of the phosphoric ester seems to be reduced.

After the phosphoric ester having an acid value is treated with the organic ortho-acid ester as described above, it is preferred, if necessary, that the treated liquid be washed with water. By washing with water, the unreacted organic ortho-acid ester is hydrolyzed and removed.

Where washing with water is conducted, a single washing operation would be enough. The amount of water for washing is adequately about 10 to 200% by weight based on the total weight of the reaction mixture. Specifically, the washing operation is carried out by, for example, adding water to the treated liquid resulting from the treatment of the crude phosphoric ester with the organic ortho-acid: ester, mixing by stirring, and allowing the mixture to stand to let the mixture separate into an aqueous layer and an oily layer, and separating and removing the upper aqueous layer by means of a separatory funnel, etc.

After washing with water, the residual water is removed to give a purified phosphoric ester. The residual water can be removed by methods generally employed in the art but preferably by distillation under reduced pressure. The distillation temperature is preferably 80 to 160° C.

Where the crude phosphoric ester is solid, the solvent that has been used for dissolving it may be removed simultaneously with the distillation under reduced pressure. The solvent can also be removed by dehydration by drying followed by steam distillation.

The thus purified phosphoric ester contains substantially no impurities, has a low acid value, and is excellent in physical properties such as heat resistance, storage stability and hydrolysis resistance.

Having a low acid value, the phosphoric esters purified by the process of the present invention, when used as a plasticizer or a flame retardant for resins, neither cause reduction of physical properties of the resins nor corrode a metallic mold used for molding the resins. Having excellent heat resistance, they undergo no compositional change at molding temperatures and no coloration. Therefore, they are suitably used as a plasticizer or a flame retardant for resins.

The present invention will now be illustrated in greater detail by way of Examples, but the present invention is not construed as being limited thereto.

Synthesis Example 1

Synthesis of Compound A (Crude Phosphoric Ester)

Phosphorus oxychloride (613 g) and bisphenol A (228 g) were allowed to react under atmospheric pressure in the presence of magnesium chloride as a catalyst. After excess of phosphorus oxychloride was removed by evaporation, phenol (376 g) was added to the residue, and the reaction was further continued under reduced pressure until a theoretical amount of hydrochloric acid was generated. The reaction mixture was diluted with xylene and washed with a hydrochloric acid aqueous solution to remove the catalyst. The reaction mixture was refluxed under reduced pressure to remove the water content to give compound A (658 g). The resulting composition was a pale yellow viscous liquid having an acid value of 1.02.

Synthesis Example 2

Synthesis of Compound B (Crude Phosphoric Ester)

Phosphorus oxychloride (460 g) and resorcin (110 g) were allowed to react under atmospheric pressure in the presence of aluminum chloride as a catalyst. After excess of phosphorus oxychloride was removed by evaporation, phenol (329 g) was added to the residue, and the reaction was further continued under reduced pressure until a theoretical amount of hydrochloric acid was generated. The reaction mixture was diluted with xylene and washed with a hydrochloric acid aqueous solution to remove the catalyst. The reaction mixture was refluxed under reduced pressure to remove the water content to give compound B (517 g). The resulting composition was a pale yellow viscous liquid having an acid value of 1.96.

EXAMPLE 1

Triethyl orthoformate (7.1 g) was added to compound A (658 g) obtained in Synthesis Example 1, and the mixture was allowed to react at 120° C. for 2 hours. After the temperature dropped to 80° C., the reaction mixture was washed with 200 g of water. The oily layer was distilled under reduced pressure to remove the water content to obtain purified product A, which was a pale yellow viscous liquid having an acid value of 0.04.

EXAMPLE 2

Triethyl orthoacetate (7.8 g) was added to compound A (658 g) obtained in Synthesis Example 1, and the mixture was allowed to react at 120° C. for 2 hours. After the temperature dropped to 80° C., the reaction mixture was washed with 200 g of water. The oily layer was distilled under reduced pressure to remove the water content to obtain purified product B, which was a pale yellow viscous liquid having an acid value of 0.03.

EXAMPLES 3 AND 4

The same procedures of Example 1 were carried out, except that an organic ortho-acid ester was allowed to react under the temperature and time conditions shown in Table 1, to obtain purified products C and D, which were pale yellow viscous liquids having an acid value of 0.08 and 0.03, respectively.

EXAMPLE 5

Triethyl orthoformate (4.4 g) was added to compound B (517 g) obtained in Synthesis Example 2, and the mixture was allowed to react at 120° C. for 2 hours. After the temperature dropped to 80° C., the reaction mixture was washed with 200 g of water. The oily layer was distilled under reduced pressure to remove the water content to obtain purified product E, which was a pale yellow viscous liquid having an acid value of 0.06.

EXAMPLE 6

The same procedures of Example 5 were carried out, except for increasing the amount (6.6 g) of triethyl orthoformate to 1.5 times as much as that used in Example 5 and changing the reaction time to 1 hour, to obtain purified product F, which was a pale yellow viscous liquid having an acid value of 0.06.

Comparative Example 1

The compound obtained in Synthesis Example 1 was distilled under reduced pressure to remove the solvent. The resulting product was designated purified product G. It was a pale yellow viscous liquid having an acid value of 1.02.

Comparative Example 2

Propylene oxide (7.1 g) was added to compound A (658 g) obtained in Synthesis Example 1, and the mixture was allowed to react at 1 20° C. for 2 hours. After the temperature dropped to 80° C., the reaction mixture was washed with 200 g of water and then heat treated at 140° C. for 30 minutes. The reaction mixture was distilled under reduced pressure to remove the water content to obtain purified product H, which was a pale yellow viscous liquid having an acid value of 0.08.

Comparative Example 3

The procedures of Comparative Example 2 were repeated, except that the heat treatment of Comparative Example 2 was not conducted, to obtain purified product I. Purified product I was a pale yellow viscous liquid having an acid value of 0.09.

In Table 1 are shown the physical property (acid value) of the purified products obtained in Examples 1 to 6 and Comparative Examples 1 to 3, the acid value after a heat resistance test at 80° C. for 14 days, and the coloration (hue) after a heat resistance test at 250° C. for 3 hours. The heat resistance test was carried out by setting a desiccator containing water in a thermostat.

TABLE 1

| | Organic Ortho-acid Ester or Epoxy Compound | Reaction Temp. (° C.) | Reaction Time (hr) | Heat Treatment | Acid Value after Purification | Heat Resistance Test Acid Value (80° C. × 14 dys) | Hue (Gardner Scale) (250° C. × 3 hrs) |
|---|---|---|---|---|---|---|---|
| Example 1 | triethyl orthoformate | 120 | 2.0 | un-done | 0.04 | 0.3 | 4 |
| Example 2 | triethyl orthoacetate | 120 | 2.0 | un-done | 0.03 | 0.4 | 4 |
| Example 3 | triethyl orthoformate | 90 | 3.0 | un-done | 0.09 | 0.3 | 4 |
| Example 4 | triethyl orthoformate | 140 | 1.0 | un-done | 0.03 | 0.3 | 4 |
| Example 5 | triethyl orthoformate | 120 | 2.0 | un-done | 0.06 | 0.8 | 5 |
| Example 6 | triethyl orthoformate | 120 | 1.0 | un-done | 0.06 | 0.7 | 5 |
| Comp. Example 1 | none | — | — | un-done | 1.02 | 2.0 | 6 |
| Comp. Example 2 | propylene oxide | 120 | 2.0 | done | 0.08 | 1.0 | 8 |
| Comp. Example 3 | propylene oxide | 120 | 2.0 | un-done | 0.09 | 1.8 | 11 |

It is apparent from the results of Table 1 that the phosphoric esters produced by the process of the present invention have a lower acid value and show a reduced rate of increase of acid value in the heat resistance test than those produced by the process of Comparative Examples (conventional production processes) and are therefore excellent in storage stability. Further, they undergo less coloration in the heat resistance test as compared with the comparative phosphoric esters. Thus, they are suit ably used as a plasticizer or a flame retardant for resins. It was additionally confirmed that the process of the present invention is simpler, involving no water/heat treatment.

Industrial Applicability

According to the production process of the present invention, high purity phosphoric. esters having a low acid value and excellent in physical properties such as heat resistance, hydrolysis resistance and storage stability can be obtained from crude phosphoric esters through simple operations.

What is claimed is:

1. A process for producing a purified phosphoric ester having a low acid value, which comprises: treating a crude phosphoric ester having an acid value with an organic ortho-acid ester, wherein said crude phosphoric ester is a phosphoric ester represented by formula (1):

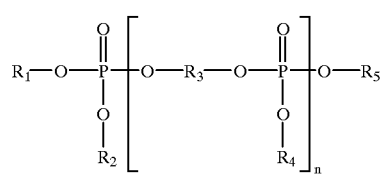

(1)

wherein $R_1$, $R_2$, $R_4$, and $R_5$, which may be the same or different, each represent an alkyl group having 1 to 10 carbon atoms or an aromatic group represented by formula (2) shown below; $R_3$ represents a divalent aromatic group represented by formula (3) or (4) shown below; and n represents 0 to 30

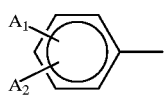

(2)

wherein $A_1$ and $A_2$ each independently represent a hydrogen atom or an alkyl group having 1 to 10 carbon atoms

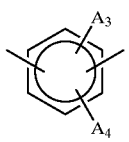

(3)

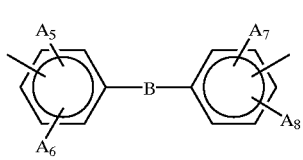

(4)

wherein $A_3$, $A_4$, $A_5$, $A_6$, $A_7$, and $A_8$ each independently represent a hydrogen atom, an alkyl group having 1 to 4 carbon atoms, a cycloalkyl group, an aryl group, an alkoxy group, a nitro group, a halogen atom or a cyano group; and B represents a single bond, divalent S, a sulfone group, or an alkylidine or alkylene group having 1 to 5 carbon atoms.

2. The process for producing a purified phosphoric ester having a low acid value according to claim 1, wherein n in formula (1) is 1 or greater.

3. The process for producing a purified phosphoric ester having a low acid value according to claim 2, wherein, in formula (1) , $R_1$, $R_2$, $R_4$, and $R_5$ are each the group represented by formula (2), $R_3$ is the group represented by formula (4), and B is 2,2'-propylidene.

4. The process for producing a purified phosphoric ester having a low acid value according to claim 3, wherein $A_1$ and $A_2$ in the group represented by formula (2) and $A_5$, $A_6$, $A_7$, and $A_8$ in the group represented by formula (4) are each a hydrogen atom.

5. The process for producing a purified phosphoric ester having a low acid value according to claim 2, wherein, in formula (1) , $R_1$, $R_2$, $R_4$, and $R_5$ are each the group represented by formula (2), and $R_3$ is the group represented by formula (3).

6. The process for producing a purified phosphoric ester having a low acid value according to claim 1, wherein said organic ortho-acid ester is an ester of orthoformic acid, orthoacetic acid or orthopropionic acid with an alkyl group having 1 to 4 carbon atoms.

7. The process for producing a purified phosphoric ester having a low acid value according to claim 1, wherein said organic ortho-acid ester is used in an amount of 1 to 20 mol per acid value of the crude phosphoric ester.

8. The process for producing a purified phosphoric ester having a low acid value according to claim 1, wherein the treating is carried out at a temperature ranging from 50° C. to 160° C.

9. The process for producing a purified phosphoric ester having a low acid value according to claim 1, wherein the treating is carried out for a period of time ranging from 10 minutes to 3 hours.

10. The process for producing a purified phosphoric ester having a low acid value according to claim 1, wherein the treating is carried out at a ratio of crude phosphoric ester to organic ortho-acid ester ranging from 1:1 to 1:20 by mole based on the acid value of the crude phosphoric ester.

* * * * *